United States Patent
Vrouwenvelder et al.

(10) Patent No.: US 11,651,243 B2
(45) Date of Patent: May 16, 2023

(54) USING MACHINE LEARNING TO EVALUATE DATA QUALITY DURING A CLINICAL TRIAL BASED ON PARTICIPANT QUERIES

(71) Applicant: International Business Machines Corporation, Armonk, NY (US)

(72) Inventors: Adrian Vrouwenvelder, Chapel Hill, NC (US); Kimberly Diane Kenna, Cary, NC (US); Stephen Alan Carraway, Durham, NC (US); John Hefferman, Durham, NC (US)

(73) Assignee: Merative US L.P., Ann Arbor, MI (US)

( * ) Notice: Subject to any disclaimer, the term of this patent is extended or adjusted under 35 U.S.C. 154(b) by 402 days.

(21) Appl. No.: 15/931,745

(22) Filed: May 14, 2020

(65) Prior Publication Data

US 2021/0357778 A1 Nov. 18, 2021

(51) Int. Cl.
| | |
|---|---|
| *G06N 7/00* | (2006.01) |
| *G06N 5/04* | (2023.01) |
| *G06N 20/00* | (2019.01) |

(52) U.S. Cl.
CPC .............. *G06N 5/04* (2013.01); *G06N 20/00* (2019.01)

(58) Field of Classification Search
CPC ......... G16H 10/20; G16H 40/20; G16H 50/20
(Continued)

(56) References Cited

U.S. PATENT DOCUMENTS

| | | | |
|---|---|---|---|
| 6,925,599 B2* | 8/2005 | Wood ..................... | G16H 10/20 715/229 |
| 7,415,447 B2 | 8/2008 | Shiffman et al. | |
| | (Continued) | | |

FOREIGN PATENT DOCUMENTS

| | | |
|---|---|---|
| WO | 2015102844 A1 | 7/2015 |
| WO | 2019182297 A1 | 9/2019 |
| WO | 2020033754 A1 | 2/2020 |

OTHER PUBLICATIONS

Getz et al., "Assessing Patient Participation Burden Based on Protocol Design Characteristics", Therapeutic Innovation & Regulatory Science 2020, vol. 54(3) 598-604. (Year: 2020).
(Continued)

*Primary Examiner* — William J Deane, Jr.
(74) *Attorney, Agent, or Firm* — Edell, Shapiro & Finnan, LLC

(57) ABSTRACT

A method, computing platform, and computer program product are provided for evaluating data quality during a clinical trial. A computing platform receives, for a clinical trial, study design information including a set of parameters and corresponding parameter values related to data quality of the clinical trial. During the clinical trial, the computing platform receives query-related information associated with queries from at least some of a plurality of participants of the clinical trial. The computing platform applies the study design information and the query-related information to at least one trained machine learning model to calculate a predicted data quality score indicating data quality for the clinical trial. At least one suggestion for improving the data quality is determined and the predicted data quality score and the at least one suggestion for improving the data quality are output.

20 Claims, 8 Drawing Sheets

(58) Field of Classification Search
USPC .......................................... 705/2; 706/12, 52
See application file for complete search history.

(56) References Cited

U.S. PATENT DOCUMENTS

| | | | |
|---|---|---|---|
| 8,032,545 | B2 | 10/2011 | Setimi |
| 8,386,416 | B2 | 2/2013 | Levin, II et al. |
| 8,793,145 | B2 | 7/2014 | Kahn et al. |
| 9,600,637 | B2 | 3/2017 | Harder et al. |
| 9,881,062 | B2* | 1/2018 | Shiftman .......... G06F 16/24575 |
| 10,255,273 | B2 | 4/2019 | Chakraborty et al. |
| 10,366,781 | B1 | 7/2019 | Menon et al. |
| 11,316,944 | B2* | 4/2022 | Bromand ........... H04N 21/4331 |
| 11,328,796 | B1 | 5/2022 | Jain et al. |
| 2004/0152056 | A1* | 8/2004 | Lamb ..................... G09B 23/28 434/262 |
| 2005/0256380 | A1 | 11/2005 | Nourie et al. |
| 2006/0036471 | A1 | 2/2006 | Sanjay-Gopal et al. |
| 2006/0129326 | A1 | 6/2006 | Braconnier et al. |
| 2006/0282244 | A1 | 12/2006 | Chotai et al. |
| 2007/0294111 | A1 | 12/2007 | Settimi |
| 2008/0109455 | A1* | 5/2008 | Katz ................. G06Q 10/06393 |
| 2009/0112618 | A1 | 4/2009 | Johnson et al. |
| 2010/0114594 | A1 | 5/2010 | Schultz |
| 2010/0250273 | A1 | 9/2010 | Li |
| 2014/0074506 | A1* | 3/2014 | Oliver ..................... G16H 40/20 705/3 |
| 2014/0214441 | A1* | 7/2014 | Young .................... G16H 10/20 705/2 |
| 2014/0278469 | A1 | 9/2014 | Secci |
| 2014/0324553 | A1 | 10/2014 | Rosenberg |
| 2014/0344208 | A1* | 11/2014 | Ghasemzadeh ........ G16H 50/50 706/52 |
| 2014/0358571 | A1* | 12/2014 | Geleijnse ............... G16H 40/20 705/2 |
| 2015/0220868 | A1 | 8/2015 | Elashoff |
| 2016/0042155 | A1 | 2/2016 | Li |
| 2016/0203296 | A1* | 7/2016 | Bound ................... G16H 10/20 705/3 |
| 2017/0286627 | A1* | 10/2017 | Barhak .................. G16H 50/50 |
| 2017/0308680 | A1* | 10/2017 | Efros .................. G06F 16/9535 |
| 2018/0039763 | A1 | 2/2018 | Tidor |
| 2018/0181573 | A1 | 6/2018 | Zhao |
| 2018/0301209 | A1 | 10/2018 | Kim et al. |
| 2018/0310890 | A1 | 11/2018 | Li |
| 2019/0066822 | A1* | 2/2019 | Ramaci .................. G16H 80/00 |
| 2019/0080785 | A1 | 3/2019 | Li |
| 2019/0131001 | A1 | 5/2019 | Fox et al. |
| 2019/0206521 | A1* | 7/2019 | Walpole ................. G06N 20/00 |
| 2019/0306093 | A1 | 10/2019 | Schilling et al. |
| 2019/0311787 | A1 | 10/2019 | Graiver et al. |
| 2019/0362838 | A1* | 11/2019 | Srivastava ............... G06N 3/08 |
| 2020/0042923 | A1 | 2/2020 | Zhou et al. |
| 2020/0151627 | A1* | 5/2020 | Shukla ................... G06Q 10/04 |
| 2020/0211680 | A1* | 7/2020 | Sablinski ............... G16H 20/00 |
| 2021/0357769 | A1 | 11/2021 | Vrouwenvelder et al. |
| 2021/0358576 | A1 | 11/2021 | Vrouwenvelder et al. |

OTHER PUBLICATIONS

Borno et al., "At What Cost to Clinical Trial Enrollment? A Retrospective Study of Patient Travel Burden in Cancer Clinical Trials", The Oncologist 2018;23:1242-1249 (Year: 2018).

Medidate Solutionsm:"Using Patient Burden Evaluation to Improve Clinical Trial Planning and Execution", May 2018 White Paper, pp. 1-7. (Year: 2018).

List of IBM Patents or Patent Applications Treated as Related, filed Jun. 2, 2020.

Harrer et al., "Artificial Intelligence for Clinical Trial Design," Trends in Pharmacological Sciences, Aug. 2019, vol. 40, No. 8 (Year: 2019), 15 pages.

"Study Shows that with Clinical Trial Participation Comes the Burden of Travel," ClinEdge Staff, http://clin-edge.com/news/study-shows-that-with-clinical-trial-participation-comes-the-burden-of-travel (Year: 2018), 3 pages.

B. Pflugeisen, et al., "Assessment of clinical trial participant patient satisfaction: a call to action", Trials 17, 483 (2016). https://doi.org/10.1186/s13063-016-1616-6, 7 pages.

* cited by examiner

USING MACHINE LEARNING TO EVALUATE DATA QUALITY DURING A CLINICAL TRIAL BASED ON PARTICIPANT QUERIES

BACKGROUND

1. Technical Field

Present invention embodiments relate to evaluating data quality of a clinical trial during the clinical trial based on queries from clinical trial participants. In particular, the present invention embodiments relate to using at least one trained machine learning model to evaluate data quality based on queries from participants during a clinical trial and predict a data quality score for the clinical trial based on the evaluated data.

2. Discussion of the Related Art

Clinical study designers have difficulty designing visit schedules and visit content for a clinical trial such that a sufficient amount of data is collected without overburdening participants. Collecting too many data points as well as collecting the data points too frequently may place too much of a burden on participants such that participant recruitment and retention may be adversely affected. Collecting too few data points or collecting the data points too infrequently may adversely affect quality of collected data during the clinical trial.

At different times during a clinical trial, participants may be required to complete a survey. If a survey question is confusing to a participant, the participant may ask one or more questions regarding the survey question. If many participants ask questions regarding one or more survey questions, then the participants may be confused and may respond inappropriately to the survey questions.

SUMMARY

According to one embodiment of the present invention, a computer-implemented method for evaluating data quality during a clinical trial is provided. Study design information for the clinical trial is received and includes a set of parameters and corresponding parameter values related to data quality of the clinical trial. Query-related information associated with queries from at least some participants of the clinical trial are received during the clinical trial. The study design information and the query-related information are applied to at least one trained machine learning model to calculate a predicted data quality score indicating data quality for the clinical trial. At least one suggestion for improving the data quality is determined and the predicted data quality score and the at least one suggestion for improving the data quality are output.

According to a second embodiment of the present invention, a computing platform for evaluating data quality during a clinical trial is provided. The computing platform includes at least one processor and at least one memory connected to the at least one processor. The at least one processor is configured to receive, for the clinical trial, study design information including a set of parameters and corresponding parameter values related to data quality of the clinical trial. During the clinical trial, query-related information associated with queries from at least some participants of the clinical trial is received. The study design information and the query-related information are applied to at least one trained machine learning model to calculate a predicted data quality score indicating data quality for the clinical trial. At least one suggestion for improving the data quality is determined. The predicted data quality score and the at least one suggestion for improving the data quality are output.

According to a third embodiment of the present invention, a computer program product for evaluating data quality during a clinical trial is provided. The computer program product includes one or more computer readable storage media having program instructions collectively stored thereon. The program instructions are executable by at least one processor of the computing platform to cause the computing platform to perform a number of steps. According to the steps, study design information, which includes a set of parameters and corresponding parameter values related to data quality of the clinical trial, is received. Query-related information associated with queries from at least some participants of the clinical trial are received. The study design information and the query-related information are applied to at least one trained machine learning model to calculate a predicted data quality score indicating data quality for the clinical trial. At least one suggestion for improving the data quality is determined and the predicted data quality score and the at least one suggestion are output.

BRIEF DESCRIPTION OF THE DRAWINGS

Generally, like reference numerals in the various figures are utilized to designate like components.

DETAILED DESCRIPTION

Figure 1:
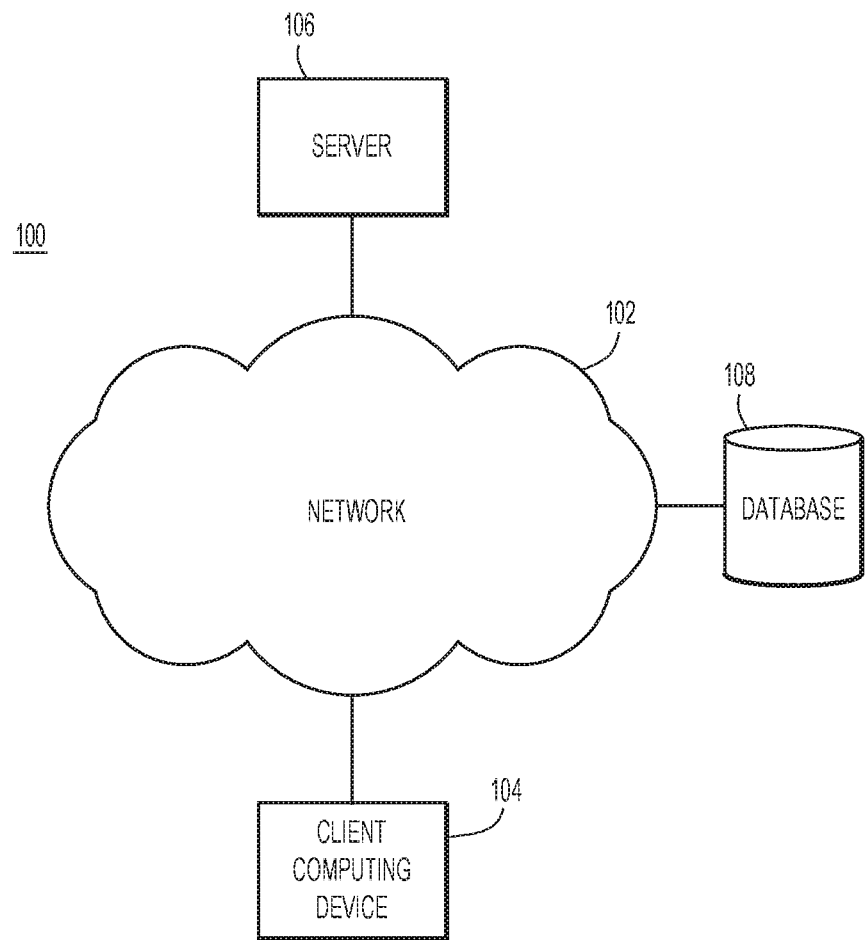
FIG. 1 is a diagrammatic illustration of an example computing environment according to an embodiment of the present invention.

In various embodiments of the present invention, at least one machine learning model is trained to evaluate data during a clinical trial and predict a data quality score based on a set of parameters and corresponding values as well as information related to queries posed by participants in the clinical trial.

Embodiments may include a number of different input parameters. For example, some of the input parameters may include meta-factors and other input parameters that may help predict a data quality score indicative of data quality of collected data from a clinical trial.

Meta-factors may determine a relevance of some parameters. Example meta-factors may include, but not be limited to, a particular therapeutic area, a specific condition, a severity of progression of a disease or a condition, and demographics. The demographics may include, but not be limited to, participant age, participant gender, family income, etc.

The input parameters that may help to predict a data quality score of a clinical trial may include, but not be limited to, a total number of participant surveys, an overall number of data points collected, participant characteristics (e.g., normalizations of age, mobility, mental acuity, etc.), respective classifications of tasks of the clinical trial, a number of questions asked per survey form, a length of questions on a survey form, types of controls used for collecting answers from participants, and answer options presented to participants where applicable.

During a study, participants may be asked to complete one or more clinical trial surveys. In some embodiments, a data quality score for a clinical trial may be predicted based, at least partly, on query-related information related to participant queries associated with the clinical trial surveys. The query-related information may include, but not be limited to, an amount of time for a participant to enter a response (e.g., a short amount of a time with respect to participant response times to similar survey questions may indicate that a question was too easy or that the participant really didn't consider the question, a long amount of time with respect to the participant response times to similar survey questions may indicate that the question was too difficult), a number of questions raised by participants per survey, a complexity of each question raised by participants (which may be indicated by question length in some embodiments), types of controls used for collecting answers (where applicable), a number of query state bounces to resolve a participant query, answer options presented to participants (where applicable), whether each participant query has been resolved, a reason why each resolved participant query has been resolved, a time duration from when respective participants ask a query and the query becomes resolved, respective contexts in which participant questions are asked, and examination of text (e.g., via natural language processing) of a response when available.

While participating in a clinical trial, participants may be asked to complete one or more on-line, computerized, or other surveys. While completing the one or more surveys, a client computing device or other computing platform may measure an amount of time that each participant takes to answer respective survey questions. If the amount of time a participant takes to answer a survey question is unusually short, compared with participant response times for similar survey questions, this may indicate that the participant did not seriously consider the survey question. If a participant's response time is unusually long, compared with participant response times for the similar survey questions, this may be an indication of participant confusion.

If a large number of questions are raised by the participants, as compared with similar clinical trials, participants may be confused and data quality of collected data from participants may suffer.

Complexity of participant questions, which may be determined by question length in some embodiments, may indicate a degree of participant confusion and may affect the quality of the collected data.

Types of controls used for collecting survey answers from participants may affect quality of collected data. Examples of such controls may include, but not be limited to, whether participants have an opportunity to discuss survey questions with other participants, whether the participants are to respond to survey questions while at a clinic or at home, etc.

A number of query state bounces may indicate a level of participant confusion regarding a survey question. For example, a participant may raise a question regarding a survey question. The participant may receive a response to the question, but doesn't fully understand the response and poses a second question (one bounce). The participant receives a response to the second question, but remains confused and poses yet another question (two bounces), etc.

During a survey, a participant may be asked to respond to a question by selecting one of a number of possible answers. The participant may not fully understand the question and may believe that none of the possible answers would be an appropriate response, but chooses the best answer among the choices, which may affect data quality of collected data.

Whether a query has been resolved and a reason for the resolution may be considered when predicting a data quality score. For example, a participant who asks a question that doesn't make sense, considering a context in which the question is asked, may be resolved because the participant has cognitive issues. In such a situation, query-related information from that participant may be discarded and may have no effect on the predicted data quality score.

Derived data may be considered when a data quality score is predicted. For example, input parameters and corresponding parameter values may provide a classification of respective tasks of a clinical trial. Further, query-related information may include a context in which a participant question is asked. In various embodiments, a classification of a task, as indicated by a context, may be compared with a classification of an immediately preceding task. Whether the two task classifications vary may be taken into consideration when predicting a data quality score. For example, if a task indicated by the context has a classification of "heart function" and an immediately preceding task has a classification of "liver function", then a participant may be confused regarding the subject matter of a survey question because the question could pertain to either heart function or liver function, which may have an effect on the data quality of collected data.

In some embodiments, task density of respective tasks of the clinical trial may be included in the input parameters. The task density may indicate a level of intensity of a task, which is an indication of whether a task is easy for a participant or difficult and painful for the participant. In such embodiments, a context in which a participant question is asked may be taken into consideration such that the computing platform may calculate a first sum of task densities of all tasks in a clinical trial and may calculate a second sum of task densities of all completed tasks of the clinical trial at a time the participant question is asked. The calculated predicted data quality may be based, at least partly, on the first sum and the second sum. For example, the computing platform may calculate a ratio of the first sum with respect to the second sum as an estimate of a percentage of the clinical trial that is completed, which may affect the predicted data quality score.

An example environment 100 for use with present invention embodiments is illustrated in FIG. 1. Specifically, environment 100 includes one or more client or end-user computing devices 104, a computing platform, which may include one or more servers 106, and a database management system 108, which may be included as part of one or more servers 106 or may be executing on a separate system connected to network 102. Server 106, client computing device 104, and database management system 108 may be remote from each other and may communicate over a network 102. Network 102 may be implemented by any number of any suitable communications media (e.g., wide area network (WAN), local area network (LAN), Internet, Intranet, etc.). Alternatively, server 106, client computing device 104, and database management system 108 may be local to each other and may communicate via any appropriate local communication medium (e.g., local area network (LAN), hardware, wireless link, Intranet, etc.).

Client computing device 104 enables a user such as, for example, a clinical study designer, to submit input parameters and corresponding parameter values for a clinical trial. The input parameters and corresponding values may be provided to client computing device 104 by the user via a user interface, which may be a graphical user interface, a textual user interface, a speech recognition user interface, or other user interface. The input parameters and the corresponding values may be provided by client computing device 104 to server 106 via network 102. Server 106 may receive the input parameters and the corresponding values and may apply the input parameters and the corresponding values to at least one machine learning model trained to predict a data quality score. Server 106 may provide client computing device 104 output from the at least one machine learning model for presentation to the user via client computing device 104. The output may include, for example, the predicted data quality score presented in a graphical format. Other embodiments may present the output in other forms such as, for example, displayed text and computer-generated speech, as well as other forms.

Database management system 108 may store various information for analysis by the at least one machine learning model such as, for example, the input parameters and their corresponding values as well as other information such as, for example, received query-related information. Database management system 108 may be implemented by any conventional or other database or storage unit, may be local to or remote from server 106 and client computing device 104, and may communicate via any appropriate communication medium (e.g., local area network (LAN), wide area network (WAN), Internet, hardware, wireless link, Intranet, etc.).

The client computing device 104 may present a graphical user interface (e.g., GUI, etc.) or other user interface (e.g., command line prompts, menu screens, etc.) to solicit information from the user pertaining to the clinical trial input parameters and the corresponding parameter values, and may provide results from applying the input parameters, the corresponding parameter values and the query-related information to the at least one machine learning model.

Figure 2:
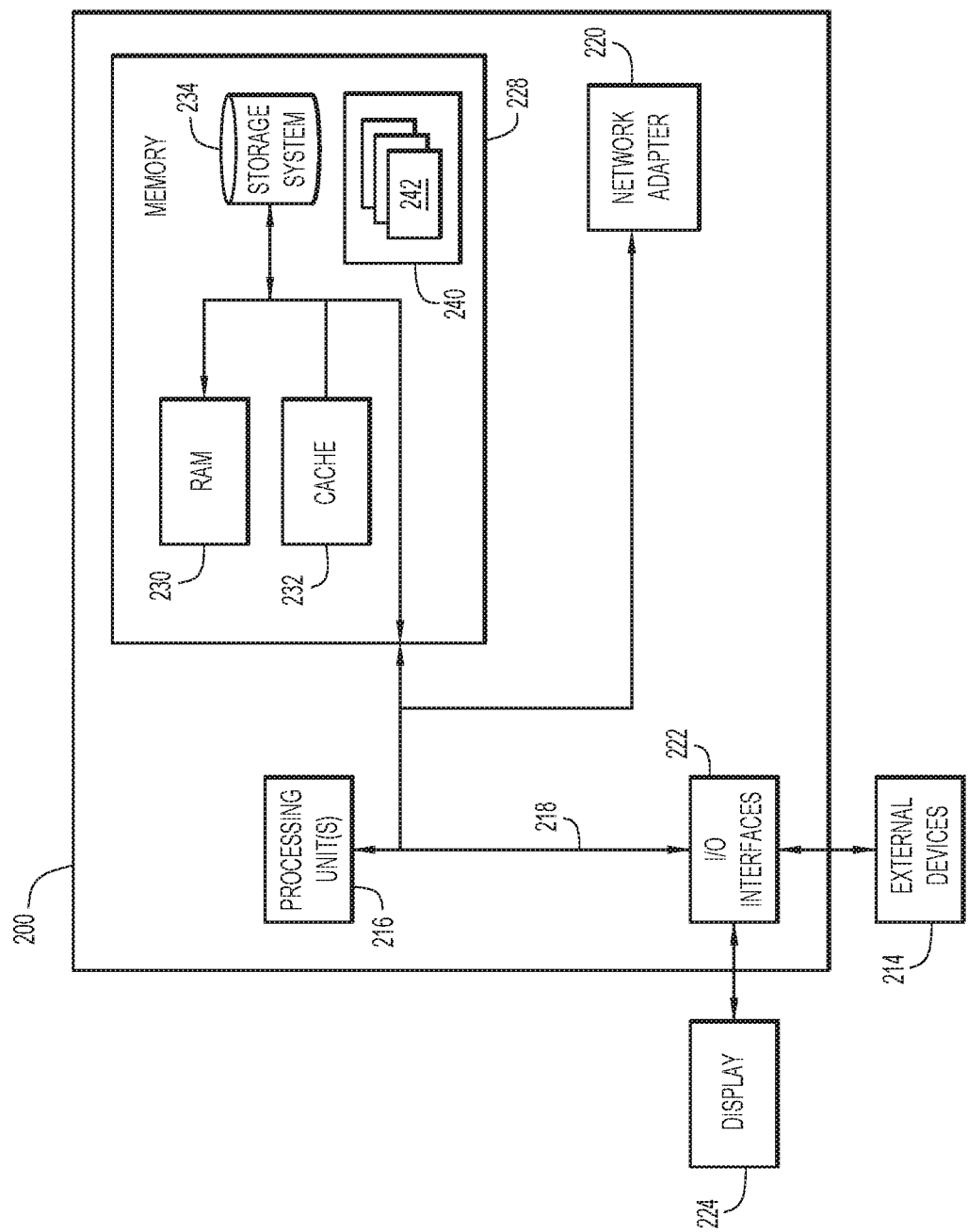
FIG. 2 is a block diagram of an example computing device according to an embodiment of the present invention.

Referring now to FIG. 2, a schematic of an example computer system 200 is shown, which may implement any of server 106 and client computer device 104 in various embodiments. Computer system 200 is shown in a form of a general-purpose computing device. Components of computer system 200 may include, but are not limited to, one or more processors or processing units 216, a system memory 228, and a bus 218 that couples various system components including system memory 228 to one or more processing units 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 200 may include a variety of computer system readable media. Such media may be any available media that is accessible by computer system 200, and may include both volatile and non-volatile media, removable and non-removable media.

System memory 228 can include computer system readable media in the form of volatile memory, such as random access memory (RAM) 230 and/or cache memory 232. Computer system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computer system 200 may also communicate with one or more external devices 214 such as a keyboard, a pointing device, one or more displays 224, one or more devices that enable a user to interact with computer system 200, and/or any devices (e.g., network card, modem, etc.) that enable computer system 200 to communicate with one or more other computing devices. Such communication can occur via Input/Output (I/O) interfaces 222. Still yet, computer system 200 can communicate with one or more networks such as a local area network (LAN), a general wide area network (WAN), and/or a public network (e.g., the Internet) via network adapter 220. As depicted, network adapter 220 communicates with the other components of computer system 200 via bus 218. It should be understood that, although not shown, other hardware and/or software components could be used in conjunction with computer system 200. Examples, include, but are not limited to: a microphone, one or more speakers, microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 3:
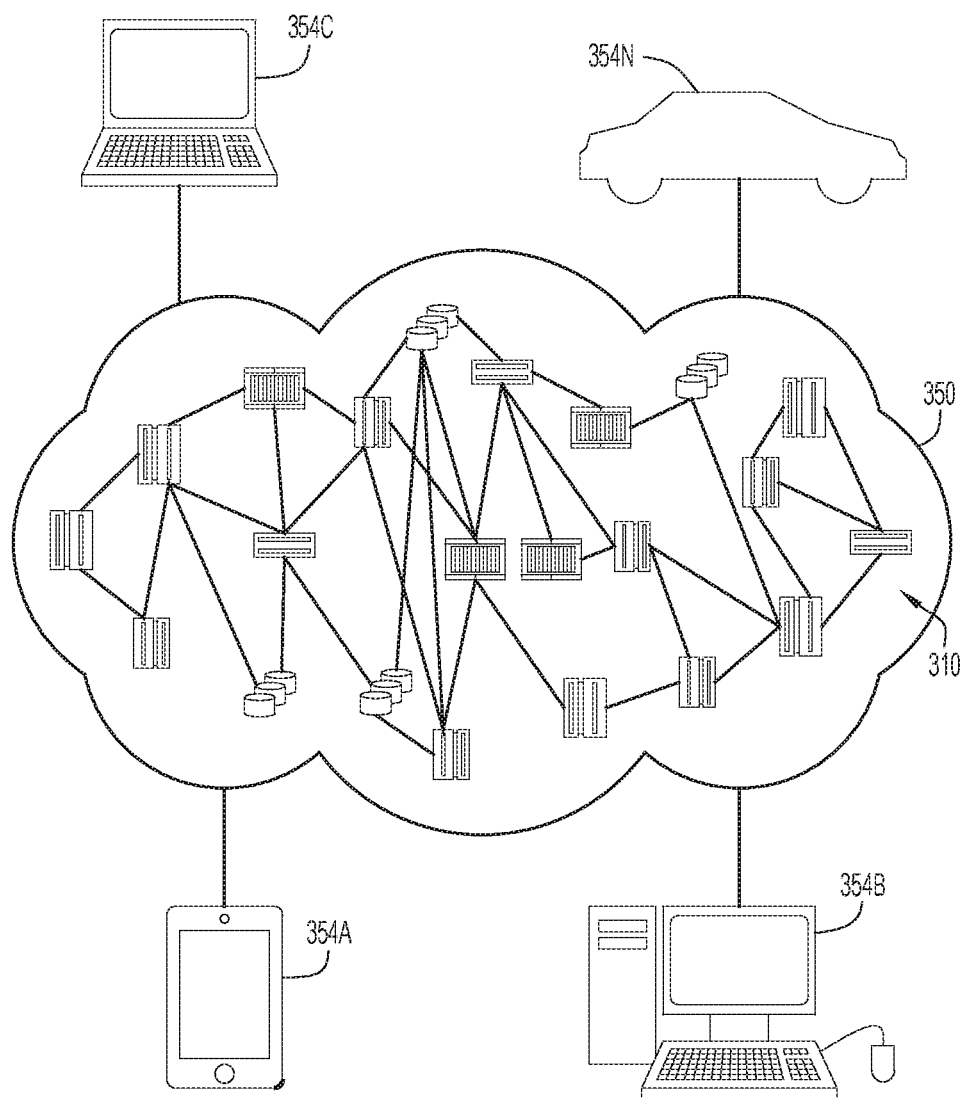
FIG. 3 illustrates an example cloud computing environment according to some embodiments of the invention.

Referring now to FIG. 3, an illustrative cloud computing environment 350 is depicted. As shown, cloud computing environment 350 includes one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
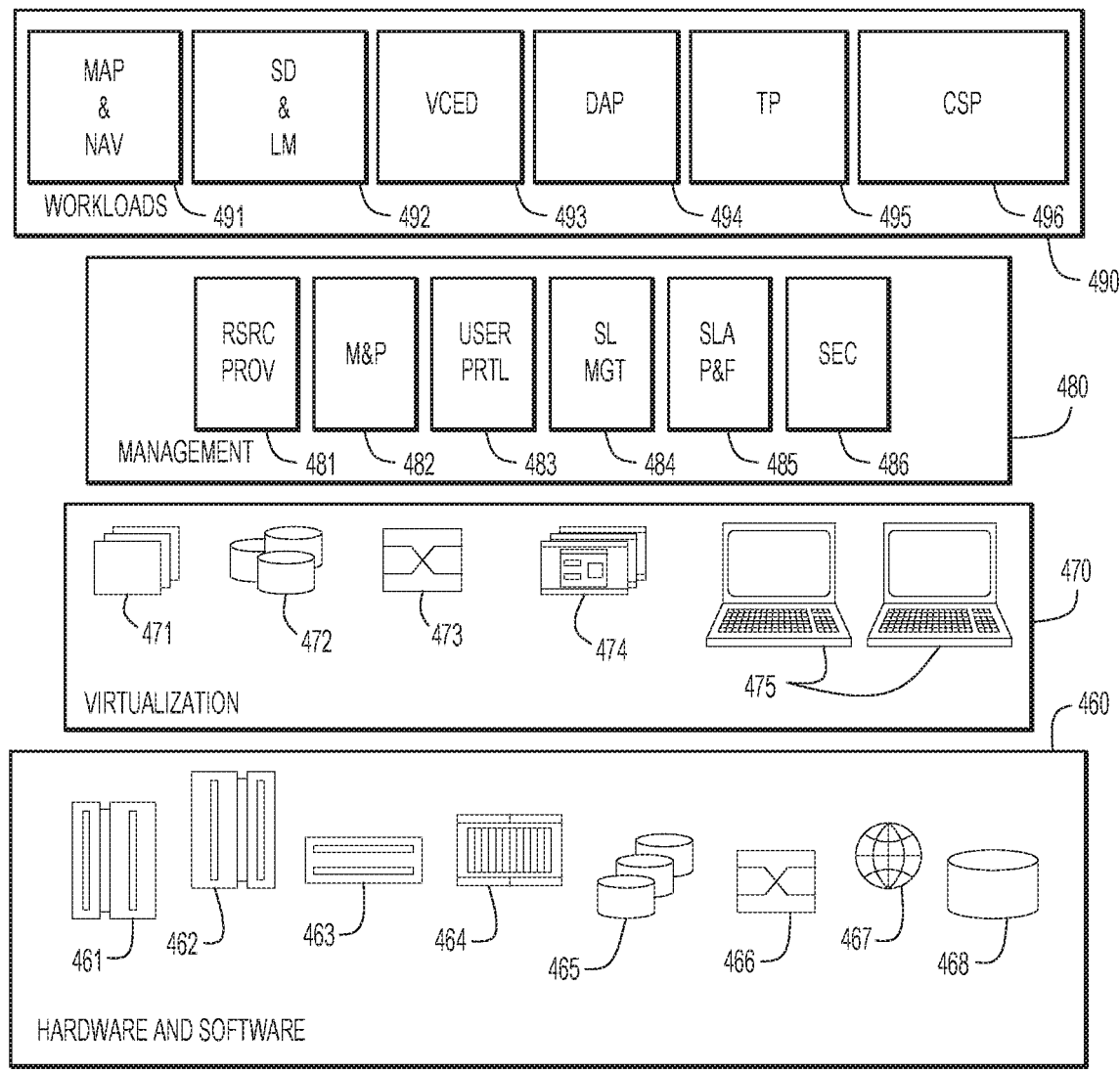
FIG. 4 illustrates an example set of functional abstraction layers that may be provided by the example cloud computing environment of FIG. 3, according to some embodiments.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example, management layer 480 may provide the functions described below. Resource provisioning 481 provides dynamic procurement of computing resources and other resources that are utilized to perform tasks within the cloud computing environment. Metering and pricing 482 provide cost tracking as resources are utilized within the cloud computing environment, and billing or invoicing for consumption of these resources. In one example, these resources may include application software licenses. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA. Security (SEC) 486 provides identity verification for cloud consumers and tasks, as well as protection for data and other resources.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; and clinical study processing (CSP) 496 for receiving input parameters and corresponding values for a clinical trial and for evaluating data quality of the clinical trial.

Figure 5:
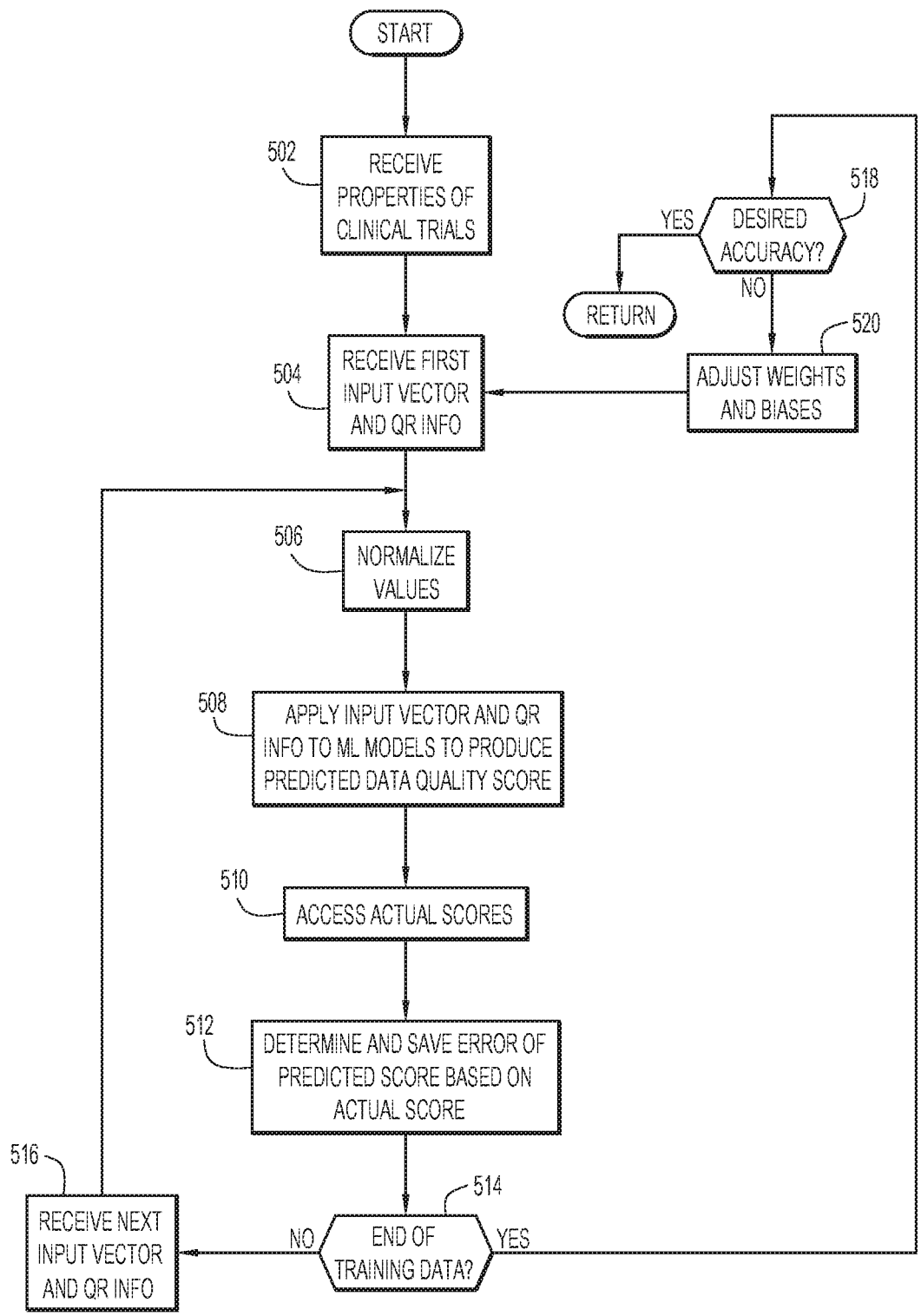
FIG. 5 is a flowchart of an example process for training one or more machine learning models according to embodiments of the present invention.

FIG. 5 is a flowchart of an example process, in various embodiments, for training one or more machine learning models to predict a data quality score for a clinical trial. This process is known as supervised machine learning. Training data includes properties of actual clinical trials and actual data quality scores related to the clinical trials. In some embodiments, a data quality score may be in a range of 0 to 100, where 0 is a worst data quality score and 100 is a best data quality score. In other embodiments, the data quality score may be in a range of 0.00 to 1.00, where 0.00 is the worst data quality score and 1.00 is the best data quality score. Other ranges for a data quality score may be employed in other embodiments of the present invention. The data quality score is a prediction of reliability, accuracy and completeness of data collected from clinical trial participants.

In some embodiments, multiple machine learning models may be used. For example, a first machine learning model may calculate a predicted data quality score based on values of the input parameters and meta-factors. A second machine learning model may calculate a predicted data quality score based on the values of the input parameters, the meta-factors, and query-related information. As an example, a first model for predicting a data quality score based on input parameters and meta-factors and which uses regression may result in $y1=B0_1+B1_1 \times x1+B2_1 \times x2+B3_1 \times x3+ \ldots Bn_1 \times xn$, where y1 is a first predicted data quality score, $B0_1$ is an offset, $B1_1$ through $Bn_1$ are coefficients, and x1 through xn represent the input parameter values and the meta-factors represented as numerical values. $B0_1$ through $Bn_1$ are derived through training the first model. An example second model for predicting a data quality score based on using query-related information may result in $y2=B0_{2a}+B0_{2b} \times y1+B1_2 \times z1+B2_2 \times z2+ \ldots Bm_2 \times zm$, where y2 is a second predicted data quality score, $B0_{2a}$ is an offset, $B0_{2b}$ and $B1_2$ through $Bm_2$ are coefficients, y1 is the first predicted data quality score, and z1 through zm are query-related information represented as numerical values.

The process may begin by receiving parameters of the clinical trials included in the training data (act 502). The parameters may be similar or identical to input parameters of clinical trials that will be applied to the one or more trained machine learning models. In some embodiments, the machine learning models may include a regression algorithm such as, for example, a linear regression algorithm. Further, the machine learning models of some embodiments may include a convolutional neural network (CNN). In other embodiments, another algorithm may be included in the machine learning model. Each of the machine learning models may include weights and a bias to be applied to values of at least some of the input parameters to calculate a predicted data quality score. The respective weights and the respective bias included in each of the one or more machine learning models may be set to predefined values initially such as, for example, zero or another value.

The one or more machine learning models may be trained based on actual clinical trials with known data quality scores. To train a machine learning model, training data may include data from a number of actual clinical trials such as, for example, 10,000 clinical trials or another number of clinical trials.

After receiving the parameters of the clinical trials, a first input vector of corresponding values of the input parameters may be received as well as query-related information (act 504). The values of the input parameters and the query-related information may be normalized (act 506). Alternatively, instead of normalizing values of the input parameters and the query-related information during the training process, the values of each input vector and the query-related information may be normalized before the training process.

Next, the received input vector and the query-related information may be applied to the machine learning model to produce a predicted data quality score (act 508).

After producing the predicted data quality score, an actual data quality score for the clinical trial may be accessed (act 510) and an error may be determined and saved based on a difference between the actual data quality score and the predicted data quality score (act 512). A determination may then be made regarding whether an end of the training data is reached (act 514) and, if not, a next input vector and query-related information for a next clinical trial in the training data may be received (act 516). Acts 506-514 then may be performed again.

If, during act 514, the end of the training data is determined to have been reached, then a determination may be made regarding whether the predicted scores are within a desired range of accuracy (act 518). If the predicted scores are determined not to be within the desired range of accuracy, then the weights and the biases for the one or more machine learning models may be adjusted to improve accuracy (act 520). Acts 504-520 again may be performed.

In some embodiments, a first machine learning model may be trained to predict a data quality score for a clinical model based on the properties of the clinical model and the corresponding values without the query-related information. This training process would differ from the training process of FIG. 5 by eliminating any reference to the query-related information. In other words, the training process would perform training using properties, corresponding values of the properties, and actual data quality scores for respective clinical trials to train the first machine learning model to predict a data quality score. In this embodiment, a second machine learning model may be trained based on the predicted data quality score from the first machine learning model, received query-related information received during clinical trials, and at least some of the properties and corresponding values of the clinical trials to predict a data quality score.

Figure 6:
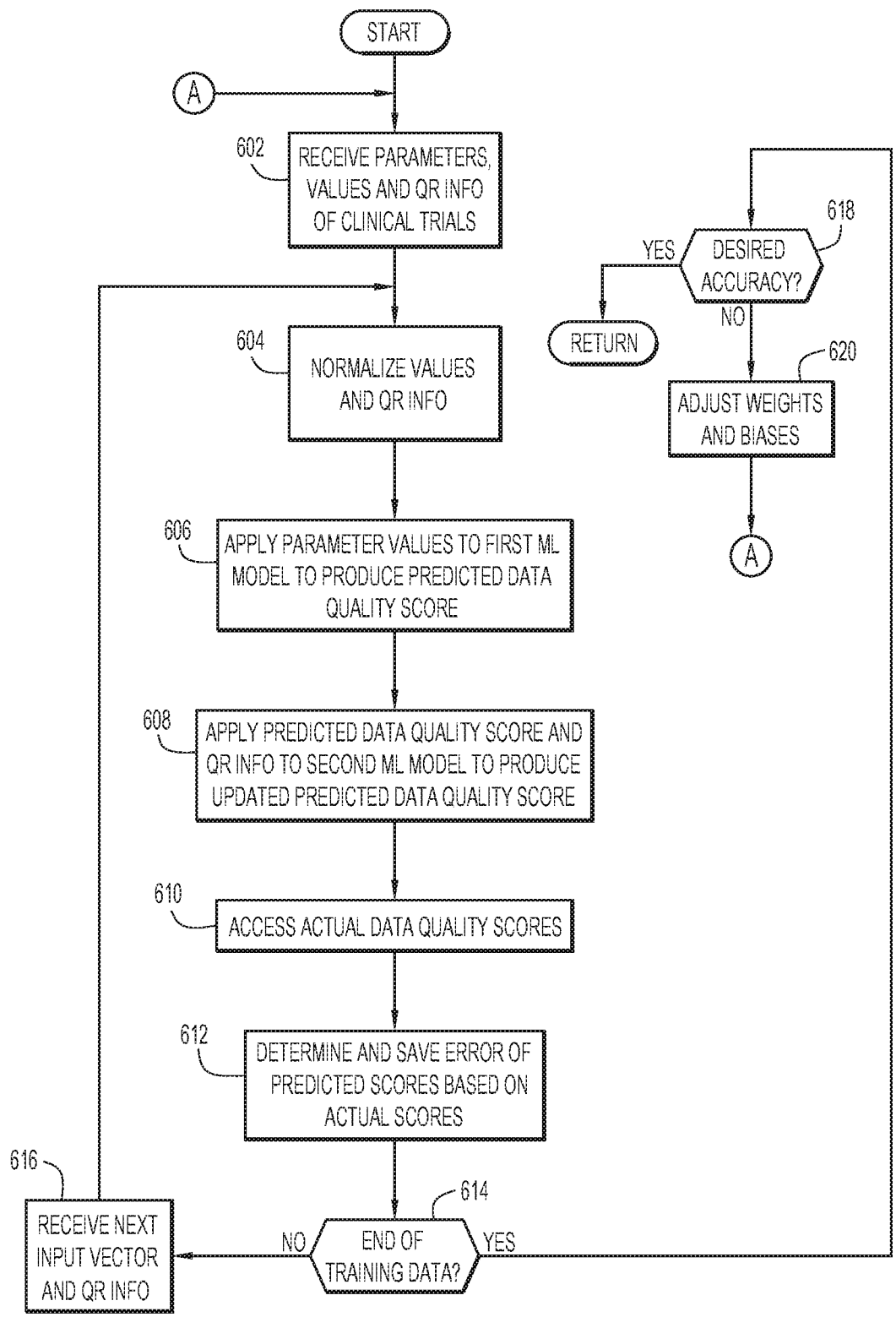
FIG. 6 is a flowchart illustrating an example process for training multiple machine learning models according to other embodiments of the present invention.

FIG. 6 is a flowchart illustrating an example process by which a second machine learning model may be trained based on a predicted data quality from a first machine learning model and query-related information from participants of clinical models. Training data may include input parameters, corresponding parameter values, query-related information from a number of clinical trials, and corresponding actual data quality scores.

The process may begin with server 106 receiving input parameters, corresponding parameter values, and query-related information for a clinical trial in a training data set (act 602). At least some of the received parameter values and the query-related information then may be normalized (act 604).

Alternatively, the at least some of the received parameter values and the query-related information in the training data set may have previously been normalized such that normalization may not be performed during training.

Server 106 then may apply the normalized parameter values to the first trained machine learning model to produce a predicted data quality score (act 606). Server 106 may then apply the predicted data quality score and the normalized query-related information to a second machine learning model to produce an updated predicted data quality score (act 608).

Server 106 may then access an actual data quality score for the clinical trial (act 610) and may determine and save an amount of error of the updated predicted data quality score based on the actual data quality score (act 612).

Server 106 may then determine whether an end of the training data set has been reached (act 614). If the end of the training data set has not been reached, then server 106 may receive a next input vector of parameter values and query-related information (act 616). Acts 604-614 again may be repeated.

If, during act 614, server 106 determines that the end of the training data set has been reached, then server 106 may determine whether the updated predicted data quality score has reached a desired level of accuracy (act 618). If the desired level of accuracy has been reached, then the process is completed. Otherwise, weights and a bias with respect to the second machine learning model may be adjusted (act 620) and acts 602-614 again may be performed.

Figure 7:
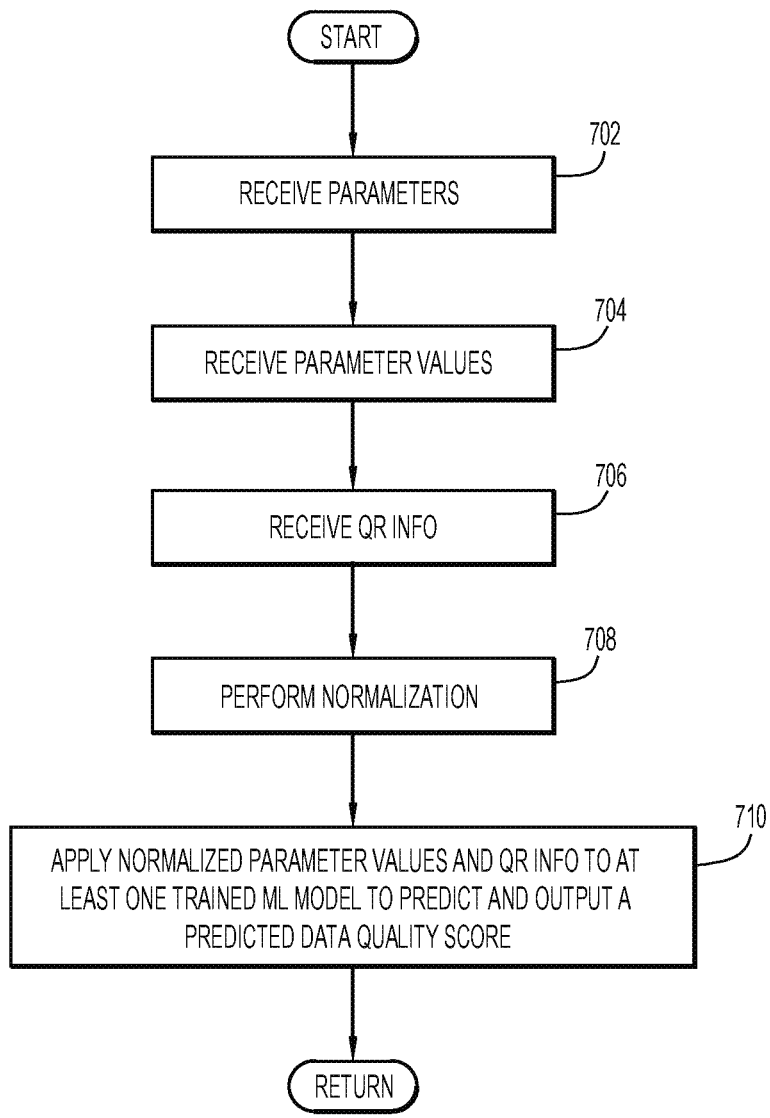
FIG. 7 illustrates a flowchart of an example process for predicting a data quality score during a clinical trial based, at least partly, on received query-related information according to embodiments of the present invention.

FIG. 7 is a flowchart illustrating an example process by which one or more trained machine learning models may be used to predict scores related to a clinical trial based on input parameters, corresponding parameter values, and query-related information associated with the clinical trial. The process may begin with server 106 receiving clinical trial input parameters (act 702) and corresponding parameter values (act 704) from client computing device 104 via network 102 (act 704). Client computing device 102 may have received the parameters and the corresponding parameter values from a user via a user interface. Server 106 may receive query-related information (act 706) and may normalize at least some of the parameter values and the query-related information (act 708). Alternatively, the parameter values and the query-related information may have been previously normalized in some embodiments. Server 106 then may execute one or more trained machine learning models to predict a data quality score for the clinical trial and may output the predicted data quality score (act 710).

Once the one or more machine learning models are trained, various parameter values and query-related information may applied to the one or more trained machine learning models to determine parameter values and query-related information that tend to improve predicted data quality scores and other parameter values and other query-related information that tend to have a detrimental effect on the predicted data quality score. Based on the above determination, various embodiments may determine recommendations for improving a predicted data quality score for a clinical study and may output the recommendations.

Figure 8:
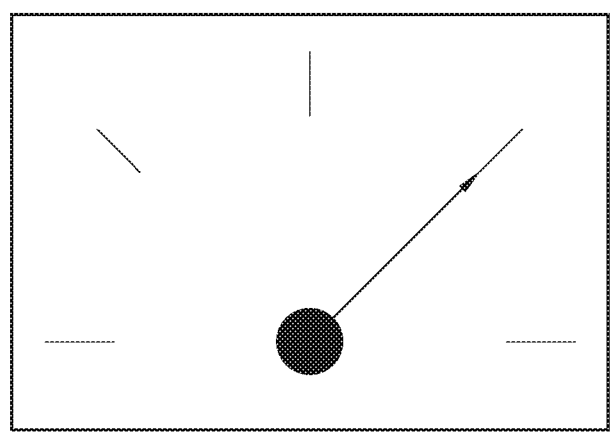
FIG. 8 illustrates an example graphical display of a predicted data quality score according to an embodiment of the present invention.

According to some embodiments, server 106 may provide a predicted data quality score to client computing device 104 such that the predicted data quality score may be presented to a user of client computing device 104 via a graphical display. The data quality score may be presented in a form that resembles a fuel gauge in an automobile. For example, FIG. 8 shows an example predicted data quality score as being about 75% or 0.75 via a graphical display.

A clinical trial may be conducted virtually (e.g., on a computer system and/or network) and/or physically for any desired item (e.g., medication, device, etc.). It will be appreciated that the embodiments described above and illustrated in the drawings represent only a few of the many ways of evaluating parameter values for a given set of clinical trial parameters and query-related information to predict a data quality score. If, during a clinical trial, a second, or updated, predicted data quality score is less than desired, the clinical trial may be amended based on one or more provided suggestions for improving data quality. Thus, the clinical trial may be amended, according to the one or more provided suggestions, while the clinical trial is ongoing to improve data quality, instead of learning after the conclusion of the clinical trial that the data quality is less than desired.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, profile generation module, profile comparison module, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information (e.g., parameters and parameter values, etc.). The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for evaluating varying sets of parameter values for a given set of parameters for a number of different projects and for providing real-time feedback including a set of the varying set of parameter values for implementing a project with a high likelihood of success.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for evaluating data quality during a clinical trial, the computer-implemented method comprising:
   receiving, by a computing platform, study design information for the clinical trial, the study design information including a set of parameters and corresponding parameter values related to data quality of the clinical trial;
   receiving, by the computing platform during the clinical trial, query-related information associated with queries pertaining to clinical trial surveys from at least some of a plurality of participants of the clinical trial;
   determining, by trained machine learning models of the computing platform, a predicted data quality score indicating data quality for the clinical trial based on the study design information and the query-related information, wherein the machine learning models are trained by training a machine learning model with training data including output from another machine learning model;
   determining, by the computing platform, at least one suggestion for improving the data quality; and
   outputting, by the computing platform, the predicted data quality score and the at least one suggestion for improving the data quality.

2. The computer-implemented method of claim 1, wherein the query-related information includes one or more from a group of a number of queries related to the clinical trial received from the at least some of the plurality of participants during the clinical trial, a complexity of each of the queries, respective time durations from when each respective query is received to when the each respective query is resolved, respective reasons regarding why the each respective query is resolved, and respective contexts in which each of the respective queries is asked.

3. The computer-implemented method of claim 2, further comprising:
   determining, by the computing platform, a respective classification of each of a plurality of tasks;
   determining, by the computing platform, respective tasks related to respective queries; and
   determining, by the computing platform, whether the respective classifications of the respective tasks related to the respective queries varies from respective classifications of corresponding immediately preceding tasks, wherein
   the predicted data quality score is based, at least partly, on whether the respective classifications of the respective tasks related to the respective queries vary from respective classifications of corresponding immediately preceding tasks.

4. The computer-implemented method of claim 2, wherein
   the query-related information includes a number of query state bounces for each of the queries.

5. The computer-implemented method of claim 1, further comprising:
   calculating, by the computing platform, a per visit task density for each of a plurality of visits for the clinical trial based on the study design information; and
   calculating, by the computing platform, a first sum of task densities of all tasks of the clinical trial and a second sum of task densities of all completed tasks of the clinical trial, wherein
   the predicted data quality score is based, at least partly, on the first sum and the second sum.

6. The computer-implemented method of claim 1, wherein:
   the query-related information includes resolution information indicating whether respective queries are resolved, and
   the resolution information includes a reason regarding why respective resolved queries are resolved.

7. The computer-implemented method of claim 1, wherein the query-related information includes data indicating whether a modification to collected data of the clinical trial occurred.

8. A computing platform for evaluating data quality during a clinical trial, the computing platform comprising:
   at least one processor; and
   at least one memory connected to the at least one processor, wherein the at least one processor is configured to:
      receive study design information for the clinical trial, the study design information including a set of parameters and corresponding parameter values related to data quality of the clinical trial;
      receive, during the clinical trial, query-related information associated with queries pertaining to clinical trial surveys from at least some of a plurality of participants of the clinical trial;
      determine, by trained machine learning models, a predicted data quality score indicating data quality for the clinical trial based on the study design information and the query-related information, wherein the machine learning models are trained by training a machine learning model with training data including output from another machine learning model;
      determine at least one suggestion for improving the data quality; and
      output the predicted data quality score and the at least one suggestion for improving the data quality.

9. The computing platform of claim 8, wherein the query-related information includes one or more from a group of a number of queries related to the clinical trial received from the at least some of the plurality of participants during the clinical trial, a complexity of each of the queries, respective time durations from when each respective query is received to when the each respective query is resolved, respective reasons regarding why the each respective query is resolved, and respective contexts in which each of the respective queries is asked.

10. The computing platform of claim 9, wherein the at least one processor is further configured to:
    determine a respective classification of each of a plurality of tasks;
    determine respective tasks related to respective queries; and
    determine whether the respective classifications of the respective tasks related to the respective queries varies from respective classifications of corresponding immediately preceding tasks, wherein
    the predicted data quality score is based, at least partly, on whether the respective classifications of the respective tasks related to the respective queries vary from respective classifications of corresponding immediately preceding tasks.

11. The computing platform of claim 10, wherein the at least one processor is further configured to:
    calculate a per visit task density for each of a plurality of visits for the clinical trial based on the study design information; and
    calculate a first sum of task densities of all tasks of the clinical trial and a second sum of task densities of all completed tasks of the clinical trial, wherein
    the predicted data quality score is based, at least partly, on the first sum and the second sum.

12. The computing platform of claim 8, wherein the at least one processor is further configured to:
    calculate a per visit task density for each of a plurality of visits for the clinical trial based on the study design information; and
    calculate a first sum of task densities of all tasks of the clinical trial and a second sum of task densities of all completed tasks of the clinical trial, wherein
    the predicted data quality is based, at least partly, on the first sum and the second sum.

13. The computing platform of claim 8, wherein:
    the query-related information includes resolution information indicating whether respective queries are resolved, and
    the resolution information includes a reason regarding why respective resolved queries are resolved.

14. The computing platform of claim 8, wherein the query-related information includes data indicating whether a modification to collected data of the clinical trial occurred.

15. A computer program product for evaluating data quality during a clinical trial, the computer program product comprising one or more computer readable storage media having program instructions collectively stored on the one or more computer readable storage media, the program instructions executable by at least one process of a computing platform to cause the computing platform to:
  receive study design information for the clinical trial, the study design information including a set of parameters and corresponding parameter values related to data quality of the clinical trial;
  receive, during the clinical trial, query-related information associated with queries pertaining to clinical trial surveys from at least some of a plurality of participants of the clinical trial;
  determine, by trained machine learning models, a predicted data quality score indicating data quality for the clinical trial based on the study design information and the query-related information, wherein the machine learning models are trained by training a machine learning model with training data including output from another machine learning model;
  determine at least one suggestion for improving the data quality; and
  output the predicted data quality score and the at least one suggestion for improving the data quality.

16. The computer program product of claim 15, wherein the query-related information includes one or more from a group of a number of queries related to the clinical trial received from the at least some of the plurality of participants during the clinical trial, a complexity of each of the queries, respective time durations from when each respective query is received to when the each respective query is resolved, respective reasons regarding why the each respective query is resolved, and respective contexts in which each of the respective queries is asked.

17. The computer program product of claim 16, wherein the program instructions are further executable by the at least one process of the computing platform to cause the computing platform to:
  determine a respective classification of each of a plurality of tasks;
  determine respective tasks related to respective queries; and
  determine whether the respective classifications of the respective tasks related to the respective queries varies from respective classifications of corresponding immediately preceding tasks, wherein
  the predicted data quality score is based, at least partly, on whether the respective classifications of the respective tasks related to the respective queries vary from respective classifications of corresponding immediately preceding tasks.

18. The computer program product of claim 15, wherein the program instructions are further executable by the at least one process of the computing platform to cause the computing platform to:
  calculate a per visit task density for each of a plurality of visits for the clinical trial based on the study design information; and
  calculate a first sum of task densities of all tasks of the clinical trial and a second sum of task densities of all completed tasks of the clinical trial, wherein
  the predicted data quality is based, at least partly, on the first sum and the second sum.

19. The computer program product of claim 15, wherein:
  the query-related information includes resolution information indicating whether respective queries are resolved, and
  the resolution information includes a reason regarding why respective resolved queries are resolved.

20. The computer program product of claim 15, wherein the query-related information includes data indicating whether a modification to collected data of the clinical trial occurred.

* * * * *